US00PP11045P

United States Patent [19]

Lambert et al.

[11] Patent Number: Plant 11,045

[45] Date of Patent: Aug. 31, 1999

[54] ANTHURIUM PLANT NAMED 'WHITE FROST'

[75] Inventors: Colon Lambert, Bowling Green; Ann E. Lamb, Sebring, both of Fla.

[73] Assignee: Sunshine Foliage World, Zolfo Springs, Fla.

[21] Appl. No.: 09/019,034

[22] Filed: Feb. 5, 1998

[51] Int. Cl.[6] ..... A01H 5/00

[52] U.S. Cl. ..... Plt./366

[58] Field of Search ..... Plt./365, 366, 369

[56] References Cited

U.S. PATENT DOCUMENTS

P.P. 10,186 1/1998 Osiecki ..... Plt./366

*Primary Examiner*—Lynette R. F. Smith
*Assistant Examiner*—Kent L. Bell
*Attorney, Agent, or Firm*—C. A. Whealy

[57] ABSTRACT

A distinct cultivar of Anthurium plant named 'White Frost', characterized by its outwardly arching growth habit; dark green glossy leaves that are deltoid in shape; numerous inflorescences that are positioned above the foliage on strong and erect peduncles; cordate pure white spathes with contrasting light pink spadices that become spotted with green as spathes age; and good post-production longevity.

2 Drawing Sheets

BACKGROUND OF THE INVENTION

The present invention relates to a new and distinct cultivar of Anthurium plant, botanically known as *Anthurium hybrid*, and hereinafter referred to by the cultivar name 'White Frost'.

The new cultivar was discovered by the co-inventor, Colon Lambert, as a naturally-occurring mutation of the *Anthurium hybrid* 'Pink Frost' (disclosed in U.S. Plant Pat. No. 8,644) and was observed in a group of tissue culture-derived plants of the parent cultivar in a controlled environment. Propagation by division and by tissue culture was accomplished by the co-inventor, Ann E. Lamb, and was used to increase the number of plants for further evaluation.

Plants of the new Anthurium are similar to plants of the parent cultivar in all observed horticultural characteristics with the exception of spathe color as plants of the new Anthurium have pure white spathes whereas plants of the cultivar 'Pink Frost' have pink spathes.

Asexual propagation of the new cultivar at Sebring, Fla., by division and by tissue culture, has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as fertlization rate, temperature and light intensity, without, however, any variance in genotype.

The following traits have been repeatedly observed and are determined to be the unique characteristics of 'White Frost'. These characteristics in combination distinguish 'White Frost' as a new and distinct cultivar:

1. Outwardly arching growth habit.
2. Dark green glossy leaves that are deltoid in shape.
3. Numerous inflorescences that are positioned above the foliage on strong and erect peduncles.
4. Cordate pure white spathes with contrasting light pink spadices. White spathes become spotted with green as spathes age.
5. Good post-production longevity.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical potted plant of 'White Frost'.

The photograph on the second sheet comprises a close-up view of typical leaves and spathes/spadices of 'White Frost'. The plant in both photographs was planted in a 20.3-cm container for about 12 months after planting a 20-week old liner propagated by tissue culture. Leaf and spathe/spadix colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Zolfo Springs and Sebring, Fla., under conditions which closely approximate commercial Anthurium production.

Botanical classification: *Anthurium hybrid* cultivar White Frost.

Parentage: Naturally-occurring mutation of *Anthurium hybrid* cultivar 'Pink Frost', disclosed in U.S. Plant Pat. No. 8,644.

Propagation:

*Method.*—By division and by tissue culture.

*Root description.*—White, fleshy roots with fine laterals. Roots growing above the soil have a light pink cast.

Plant description:

*Plant shape.*—Upright, inverted triangle, symmetrical.

*Growth habit.*—Erect when young, becoming outwardly arching as plants develop. Appropriate for 12 to 25-cm containers.

*Plant height.*—Under appropriate production conditions, plants of the new Anthurium attain a marketable size of about 34 to 40 cm in height and about 65 to 74 cm in width.

*Foliage description.*—Length: About 20.3 to 25.4 cm. Width: About 13.5 to 15.2 cm. Shape: Deltoid. Apex: Acuminate. Base: Truncate with two rounded lobes which do not extend past the petiole. The distance from the petiole/leaf junction to the hightest point on the lobes is about 6.3 to 7.6 cm. Margin: Entire, straight or somewhat wavy. Aspect: Leaf blade flat or slightly convex between veins on the upper surface. Venation: Upper surface: Midrib protruding for about two-thirds of the length of the leaf. Lateral veins, sunken. Lower surface: Prominent. Texture: Leathery and glossy. Color: Newly emerged leaves are typically flushed with bronze coloration. Upper surface: 137A/139A. Lower surface: 146B/146C. Midrib, upper surface: 146B/146C. Midrib, lower surface: 146C/146D. Petiole: Length: About 23.2 to 25.5 cm. Diameter: About 4 mm just below the geniculum. The petiole below the geniculum is straight or slightly curved. Petiole sheath: Length: About 2.7 cm, rounded at tip of sheath. Width: About 3 mm at the midpoint. Distance between top of petiole sheath and base of geniculum: About 18.6 to 22.5 cm. Color: 144A/146B. Color, petiole wing: 146B. Geniculum: Adjacent to base of leaf blade. Length: About 3.4 to 4.1 cm. Width: About 5 mm. Aspect: Often curved. Color: 146C.

Inflorescence description:

*Inflorescence arrangement.*—Spathe with spadix held above the foliage. Freely flowering, numerous inflorescences per plant that are oriented vertically. Inflorescences typically grouped in the center of the plant.

*Flowering time.*—First inflorescences are typically produced about 4 to 5 months after planting a 20-week old liner. After an additional 7 to 8 months of growth, plants will continuously develop about 5 to 8 inflorescences. Actual time to flower and number of inflorescences will depend on environmental and cultural conditions. Smaller spathes/spadices may develop on less mature growth.

*Longevity.*—Depending on time of year and maturity of the plant, spathes will maintain their aesthetic quality for about 6–8 weeks on the plant.

*Spathe.*—Immature spathes are tightly rolled around the spadices. Spathes are fully open about when the peduncle is fully elongated, spathes positioned about 32 to 40 cm above the soil surface. Size (spathe not flattened for measurements): Length: About 6.5 to 7.6 cm. Width: About 5.3 to 6 cm. Height above foliage: About 7.5 cm. Shape: Cordate. Apex: Cuspidate and hooked upwards. Base: Cordate to truncate. Margin: Entire. Texture: Leathery, glabrous. Aspect: Cupped, about 6 to 8 mm in depth, spathes do not reflex with further development. Color: Fully open: Front surface: Brighter, but closest to 155D. Back surface: 155D. Faded: Front surface: 155D with spots of green, 144A. Back surface: 155D with spots of green, 144A.

*Spadix.*—Length: About 5.2 to 5.6 cm. Diameter: About 6 mm. Shape: Columnar. Cross section: Rounded. Color: When the spathe unrolls, the spadix is lighter than but closet to 62D, darkening to 73C/73D, becoming light green, 145A, at the apex. The entire spadix becomes light green, 145B/145C, with further development.

*Peduncle.*—Aspect: Straight, erect. Strength: Strong, but wiry. Color: 144A to 146D.

*Reproductive organs.*—Androecium: Anthers and filaments are minute and not clearly visible. Pollen, white in color. Gynoecium: Translucent white, protruding between the stamens, firmly fixed to the main axil. The pistils extend about 0.5 mm beyond the stamens.

Disease resistance: Plants of the new Anthurium have demonstrated good tolerance to root pathogens common to Anthuriums.

Seed development: Seed development has not been observed.

It is claimed:

1. A new and distinct cultivar of Anthurium plant named 'White Frost', as illustrated and described.

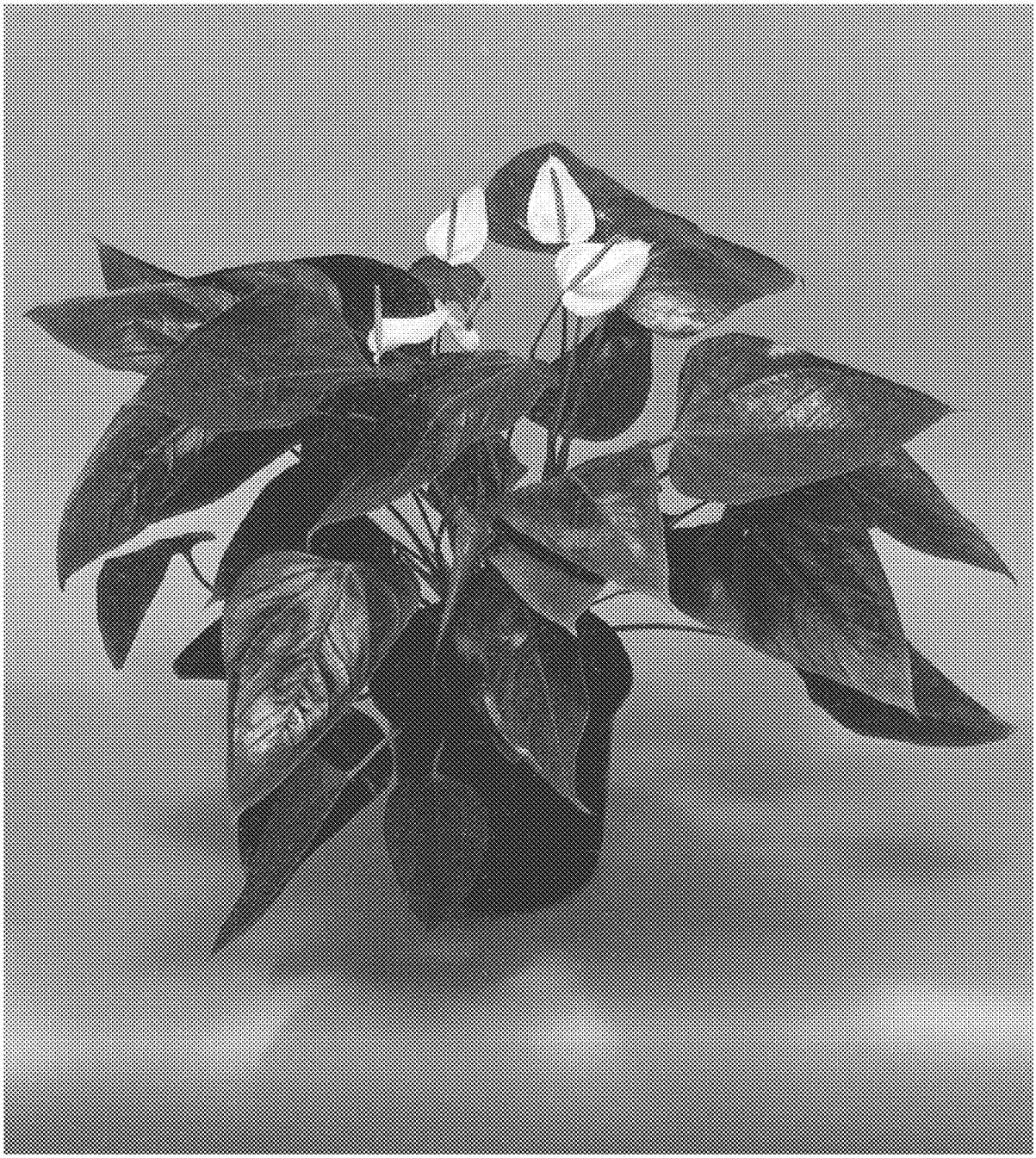

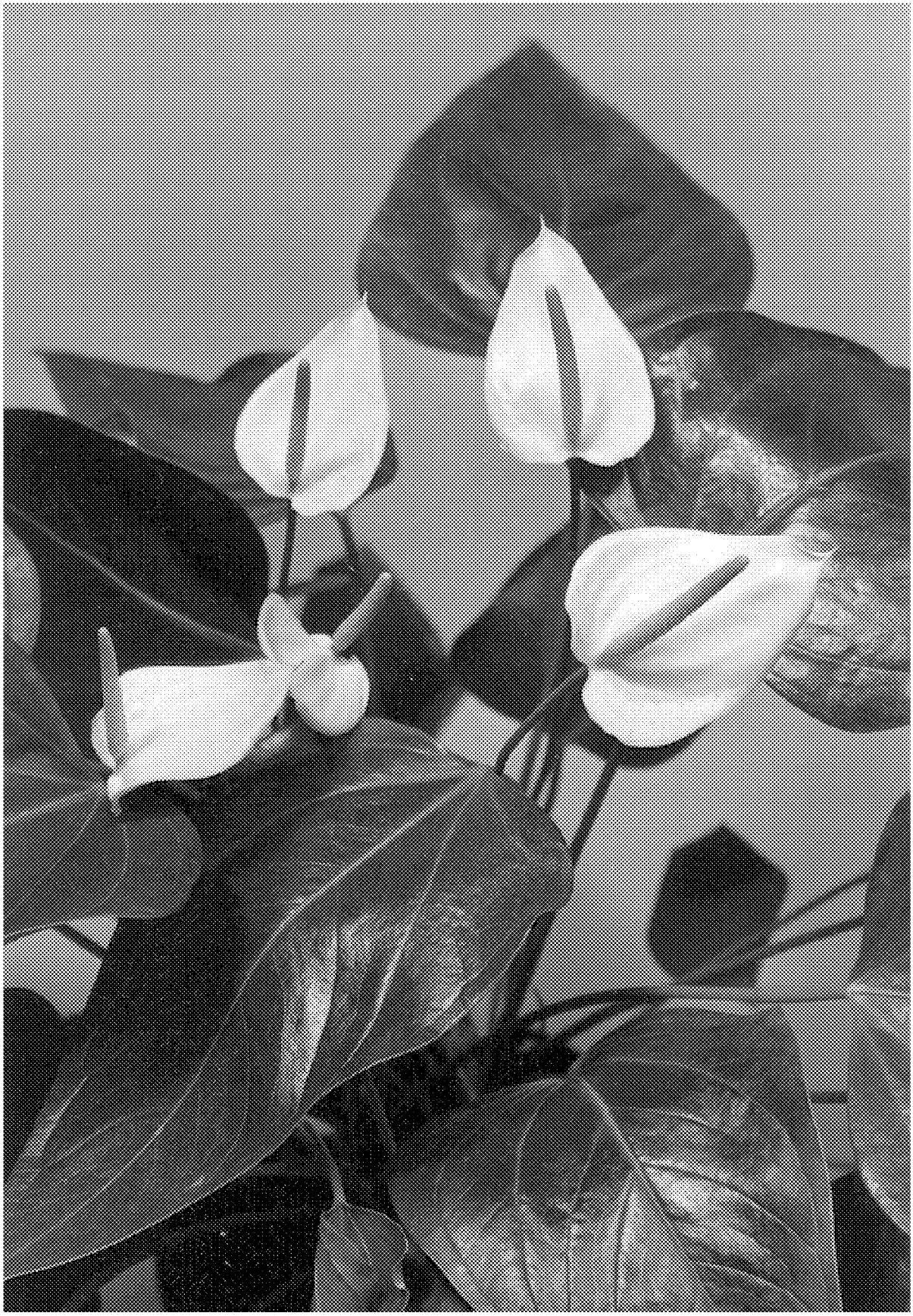

* * * * *